United States Patent [19]

Skimina

[11] Plant 5,078

[45] Aug. 2, 1983

[54] *PINUS THUNBERGIANA* SELECTION

[75] Inventor: Conrad Skimina, Upland, Calif.

[73] Assignee: Monrovia Nursery Company, Azusa, Calif.

[21] Appl. No.: 240,371

[22] Filed: Mar. 4, 1981

[51] Int. Cl.[3] ..... A01H 5/00

[52] U.S. Cl. ..... Plt./50

[58] Field of Search ..... Plt./50

*Primary Examiner*—James R. Feyrer

[57] ABSTRACT

A new and distinct variety of *Pinus thunbergiana* tree (popularly known as Japanese black pine). A specifically selected, genetically superior plant which is able to absorb more iron from the soil than other seedlings of *Pinus thunbergiana* resulting in a more uniform green color of the needles. Another distinguishing characteristic of this selection is the absence of needle tip burn (or browning) associated with smog.

2 Drawing Figures

DISCOVERY

This invention relates to a new and distinct variety of *Pinus thunbergiana,* a member of the Pinaceae family. This new variety was a deliberate selection by Mr. Conrad Skimina from a seedling bed of *Pinus thunbergiana* at Monrovia Nursery Company, 18331 E. Foothill Boulevard, Azusa, Calif. on May 1, 1976 (See FIG. 1).

The plant to date is known to exist only within the boundaries of Monrovia Nursery and has not been offered for sale or described in any publication.

REPRODUCTION

This new selection was chosen from seedlings which were phenotypically variable. The new selection has genetic attributes that differ from the other seedlings. In order to retain the genetic attributes of the new selection, propagation at Monrovia Nursery Company has been restricted to asexual reproduction by vegetative cuttings. Sexual reproduction, such as seed propagation, would result in a potential loss of the selected genetic attributes. Seed progeny from the new selection has not been observed.

CHARACTERISTICS

This new selection differs from other seedlings of *Pinus thunbergiana* in the following respects:

(1) The needle color is uniform while the seedlings have a wide range of colors — including "chlorotic" (yellow) needles. This chlorosis exhibited by seedlings is due to a genetic inability to extract iron from the soil. When both plants are grown in the same soil, tissue analysis revealed that the tissue of new selection had 99 parts/million of iron while tissue of the seedlings contained an average of only 68 parts/million of iron. Even when the new selection was grown in a soil with less available iron than the soil the seedlings were grown in, the selection absorbed more iron. Proving the genetic superiority of the selection and its efficiency to extract iron from the soil.

(2) The new selection does not exhibit any tip burn (necrosis) associated with smog, whereas seedlings exhibit a wide variation with little to severe tip burn (see illustration-FIG. 2). Both the seedlings and the selection were grown in the same location and were exposed to last year's smog which resulted in damage to the seedlings but did not result in damage to the new selection.

The new selection was deliberately made to achieve genetic uniformity, to reduce the presence of yellow needles by an increased ability to uptake iron from the soil and to eliminate tip burn on needles associated with smog. Both research and appearance prove that when compared to other seedlings this genetically superior selection has a greater uptake of iron resulting in uniform green needle color and a resistance to tip burn associated with smog. These attributes are important not only aesthetically but also for the health, vigor and growth of the plants.

BRIEF DESCRIPTION OF THE DRAWING

The left photo, labeled prior art, depicts a typical specimen showing characteristic susceptibility of the species to smog damage; the photo on the right, designated selection shows a specimen of the selected plant growth under similar exposure to smog but having little or no smog needle tip burn.

DESCRIPTION

Below is a detailed description of the new variety, all color terminology is from the British Horticultural Colour Charts. Overall Size and Habit: Expected growth will be similar to *Pinus thunbergiana* seedlings. Needle:

Number: 2, characteristic of this species.
Length: Variable, $5\frac{1}{4}''$ to $3\frac{3}{4}''$.
Fasicle: $\frac{1}{2}''$ in length, papery, persistent.
Shape: Acicular, one side flatten, sharp acuminate tip.
Color: Parsley Green 00962, exhibiting no browning of tip.

Inflorescense & Fruit: The flower and cone have not been observed.

I claim:

1. A new and distinct selection of *Pinus thunbergiana* as substantially shown and described herein, that is characterized by uniformity in color — exhibiting the absence of yellowing (chlorosis) of needles and the resistance to needle tip burn (necrosis) associated with smog.

* * * * *

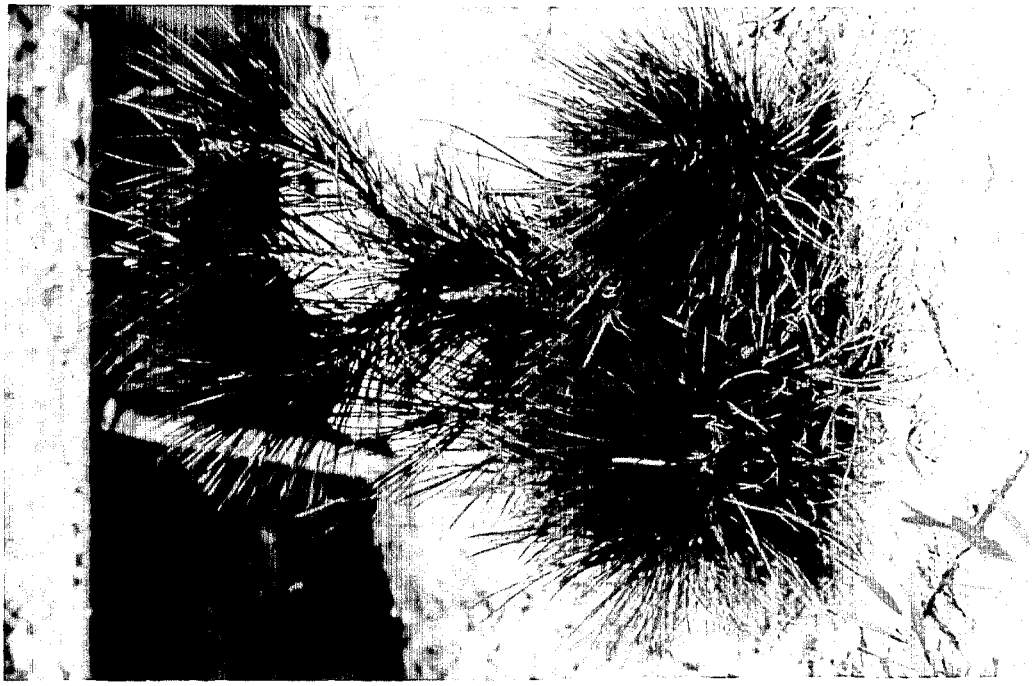
SELECTION
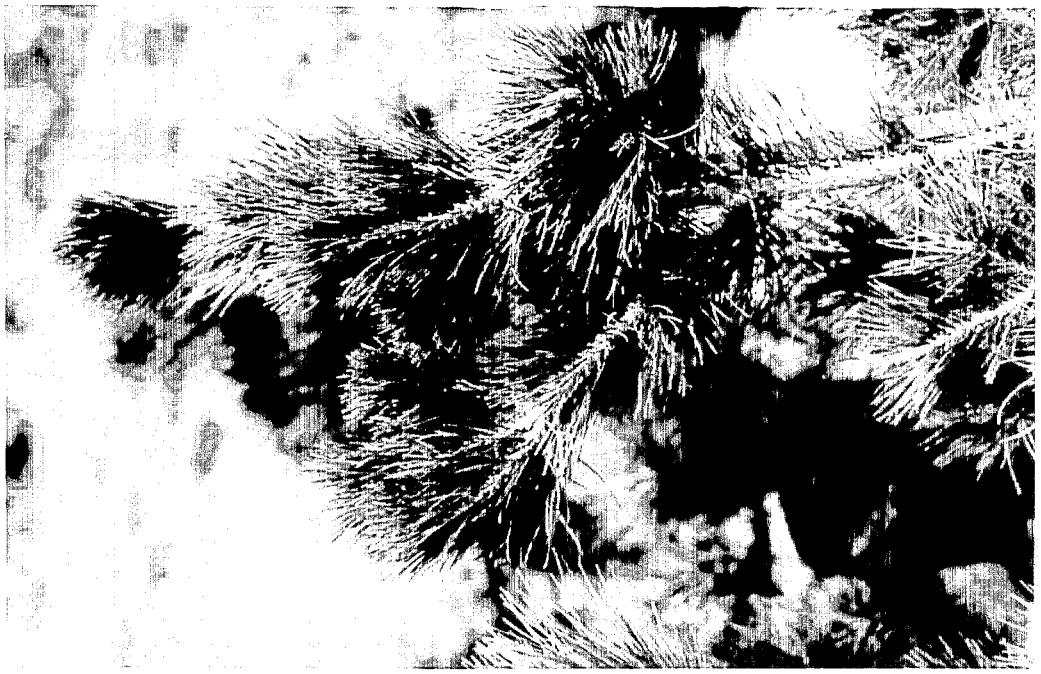
PRIOR ART